United States Patent [19]

Yokoyama et al.

[11] 4,425,347
[45] Jan. 10, 1984

[54] PERFLUOROBICYCLO COMPOUND EMULSION PREPARATION

[75] Inventors: Kazumasa Yokoyama, Toyonaka; Chikara Fukaya, Osaka; Yoshio Tsuda, Takarazuka; Taizo Ono, Osaka; Yoshio Arakawa, Suita; Yoshihisa Inoue, Kyoto; Youichiro Naito, Hirakata; Tadakazu Suyama, Kyoto, all of Japan

[73] Assignee: The Green Cross Corporation, Osaka, Japan

[21] Appl. No.: 454,105

[22] Filed: Dec. 28, 1982

[30] Foreign Application Priority Data

Sep. 9, 1982 [JP] Japan .................................. 57-157677

[51] Int. Cl.³ .......................................... A61K 31/435
[52] U.S. Cl. .................................................. 424/256
[58] Field of Search ............... 424/256, 258, 350, 352; 546/138

[56] References Cited

U.S. PATENT DOCUMENTS 3,911,138 10/1975 Clark ................................. 424/352
3,962,439 6/1976 Yokoyama et al. ................. 424/352

Primary Examiner—Sam Rosen
Attorney, Agent, or Firm—Cushman, Darby & Cushman

[57] ABSTRACT

A perfluorobicyclo compound emulsion preparation having oxygen carrying ability containing a perfluorobicyclo compound of the general formula:

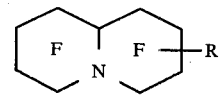

wherein R represents a perfluoromethyl group or perfluoroethyl group, as an oxygen carrying component.

6 Claims, No Drawings

PERFLUOROBICYCLO COMPOUND EMULSION PREPARATION

The presnet invention relates to therapeutical fluorocarbon emulsions having oxygen carrying ability to be used for life-saving of massively bleeding patients, storage of an organ involved in the transplantation of the organ, etc.

It has already been reported that the fluorocarbon emulsions possess the possibility of being used as red cell substitutes for mammals and as organ storing perfusates for transplantation of organs, especially as transfusions for the purpose of performing the oxygen carrying ability [Leland C. Clark, Jr., Becattini, F., Kaplan, S., The Physiology of Synthetic Blood, Journal of Thoracic Cardiovascular Surgery, Vol. 60, p. 757–773, 1970, Geyer, R. P., Fluorocarbon—Polyol Artificial Blood Substitutes, New Engl. J. Med., Vo. 289, p. 1077–1082, 1973].

However, the previously known fluorocarbon emulsions cannot be said practical because of their pharmaceutical instability, and it is necessary to develop a stable preparation in which the particle diameter does not change for a prolonged time in order to put the fluorocarbon emulsions into practical use as artificial red cells.

In the fluorocarbon emulsions, the size of the particles plays a important role on the toxicity and efficacy of the emulsion. [Yokoyama, K., Yamanouchi, K., Watanabe, M., Murashima, R., Matsumoto, T., Hamano, T., Okamoto, H., Suyama, T., Watanabe, R., Naito, R., Preparation of Perfluorodecalin Emulsion, an Approach to the Red Cells Substitute, Federation Proceeding, Vol. 34, p. 1478–1483, May, 1975]. In other words, the emulsion having a large particle diameter has high toxicity and also the retention time of the particles in the blood stream is short. Therefore, when a fluorocarbon emulsion is employed as artificial red cells for a life-saving transfusion for massively bleeding patients, the particle diameter of the emulsion particles should be $0.3\mu$ or less, preferably $0.2\mu$ or less [Japanese Patent Application "Kokai" (Laid-open) No. 22612/1973]. Apart from the particle diameter, in order to use a fluorocarbon for the purpose of artificial red cells, the fluorocarbon administered into the vein must be rapidly eliminated out of the body after finishing the original purpose of the oxygen transport (U.S. Pat. No. 3,911,138, Leland C. Clark, Jr.). Dr. Clark named such compounds as reticuloendothelial-system (RES) phobic fluorine-containing organic compounds, and distinguished these compounds from RES-philic compounds which are characterized by the presence of an atom such as oxygen or nitrogen in their structure or by their heterocyclic nature.

The present inventors have conducted extensive studies on an enormous number of compounds including perfluorobicyclo compounds of the general formula:

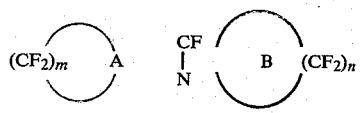
(I)

wherein either or both of Ring A and Ring B may optionally be substituted with lower perfluoroalkyl group(s), m and n each represents 3 or 4, and found that specific compounds included within the compounds, which are named as RES-philic compounds by Dr. Clark, represented by the formula (I), i.e. the perfluorobicyclo compounds of the general formula:

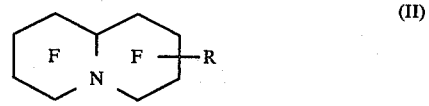
(II)

wherein R represents a perfluoromethyl group or perfluoroethyl group can yield long-term stable emulsions having extremely fine particles and moreover said compounds are unexpectedly excellent in the properties of elimination. Thus, the present invention has been accomplished.

An object of the present invention is to provide a therapeutical fluorocarbon emulsion preparation having oxygen carrying ability containing a compound represented by the above-mentioned general formula (II) as an oxygen carrying component.

Other objects and advantages of the present invention will be apparent from the following descriptions.

In relaton to the general formula (II), while the substitution position of the perfluoromethyl group is not particularly restricted, it is preferred that the number of the substituents is one.

The therapeutical perfluorocarbon emulsions having oxygen carrying ability are known per se in the art, and hence the feature of the present invention resides in the selection of the specific perfluoro-compounds, i.e. the compounds of the general formula (II) as the perfluorocarbon compound. Therefore, as the perfluorocarbon emulsion preparations themselves in the present invention, those similar to the previously known products may be contemplated. That is, they are oil-in-water emulsions in which a perfluoro-compound is dispersed in water, and the amount of the perfluoro-compound to be incorporated is 5–50% (w/v), preferably 10–40% (w/v).

On preparing an emulsion, a polymeric nonionic surfactant, a phospholipid and the like are employed each alone or in combination thereof as an emulsifying agent, and its amount to be added is 1–5% (w/v).

The polymeric nonionic surfactant used herein is that having a molecular weight of 2,000–20,000, and examples thereof include polyoxyethylene-polyoxypropylene copolymers, polyoxyethylene fatty acid esters, polyoxyethylene castor oil derivatives, etc., and examples of the phospholipid include, vitelline phospholipid, soybean phospholipid, etc.

In addition, if necessary, it is also possible to add as an emulsifying agent, for example, a fatty acid having 8–22 carbon atoms, particularly 14–20 carbon atoms, or a physiologically acceptable salt thereof (e.g. alkali metal salts such as sodium salt, potassium salt, etc., monoglycerides thereof]. Examples of the above fatty acid include caprylic acid, capric acid, lauric acid, myristic acid, palmitic acid, stearic acid, behenic acid, palmitoleic acid, oleic acid, linoleic acid, arachidonic acid, sodium or potassium salts thereof, their glycerides, etc. The amount thereof to be added is 0.001–0.01% (w/v).

As the medium, a physiologically acceptable aqueous solution, for example, physiological saline, lactic acid added Ringer's solution, etc., may be employed.

If necessary, there may be further added an isotonizing amount of an isotonizing agent such as glycerol to isotonize the emulsion, and a plasma extender such as hydroxyethylstarch, dextran, etc. to adjust the colloid osmotic pressure of the emulsion.

The emulsions of the present invention may be prepared by mixing the respective components in any order, coarsely emulsifying and homogenizing using an appropriate emulsifier (e.g. a Manton-Gaulin type emulsifier) until the particle diameter becomes $0.3\mu$ or less.

Further, the compound represented by the general formula (II) can be produced by fluorinating a perhydro-compound corresponding to the compound of the general formula (II). As the fluorination method, there may be mentioned, for example, known fluorination method such as direct fluorination method, cobalt fluorination method, electrolytic fluorination method, etc.

For the production of the compound (II), the electrolytic fluorination method is preferred, and this can be effected by, for example, mixing and dissolving anhydrous hydrofluoric acid and a perhydro-compound as starting material in an electrolytic cell, and thereafter effecting electrolysis. In said electrolysis, the voltage is generally 3–9 V, the anode current density is generally 1–300 $A/dm^2$, and the bath temperature is generally 4°–10° C.

Since the thus formed compound of the general formula (II) is insoluble in anhydrous hydrofluoric acid, it precipitates in the lower layer of the electrolytic cell.

Separation and purification of the compound (II) from said precipitates may be effected by, for example, adding a liquid mixture of an equal volume of an aqueous alkali solution and an amine compound to the recovered precipitates, separating the lowest layer containing the compound (II) (at that time, partially fluorinated compounds are separated into the amine layer), washing it with an appropriate amount of aqueous acetone containing potassium iodide to remove compounds having fluorine atoms bound to nitrogen atoms, and further subjecting to fractional distillation to separate the compound (II).

The perfluorobicyclo compound emulsion preparations according to the present invention have oxygen carrying ability, and thus are employed as, for example, transfusions for oxygen transport (the so-called red cell substitutes), organ storing perfusates, etc.

When the perfluorobicyclo compound emulsion preparation of the present invention is employed, as e.g. a transfusion for oxygen transport, it is generally administered by intravenous injection, and the dosage for a human adult is 50–2,000 ml per dose.

REFERENCE EXAMPLE 1

Preparation of perfluorobicyclo compound

As an electrolytic cell, a tank (made of Monel metal) having a capacity of 1.5 l, containing electrodes made of nickel (purity of 99.6% or higher) (6 anodes and 7 cathodes) alternately arranged with an electrode gap of 1.7–2.0 mm with an effective anode surface area of 10.5 $dm^2$ and further equipped with a reflux condenser made of copper above the tank was employed.

To this electrolytic cell was introduced 1.2 l of anhydrous hydrofluoric acid, and the impurities (water and sulfuric acid) present in very small amounts were removed by the preliminary electrolysis. Thereafter, 0.85 mole (130 g) of 4-methyloctahydroquinolidine was dissolved in the hydrofluoric acid, and while passing helium gas at a flow rate of 100 ml/min. from the lower part of the cell, the electrolysis was effected with an anode current density of 1.0–2.0 $A/dm^2$, a voltage of 4.0–6.2 V and a bath temperature of 4°–10° C. The electrolysis was continued for 1051 A·hr until the electrolytic voltage reached 9.0 V. Anhydrous hydrofluoric acid was additionally introduced 200 ml per 24 hours. The gas generated during the electrolysis was passed through an iron tube packed with sodium fluoride pellets to remove the entrained anhydrous hydrofluoric acid, and then led into a trap cooled with dry ice-acetone to liquefy and trap, to obtain 9.5 g of a colorless liquid. On the other hand, the bath solution in the electrolytic cell separated into two phases, the upper layer containing anhydrous hydrofluoric acid and the lower layer fluorobicyclo compound. The lower layer was separated and weighed 263 g.

The liquid collected by cooling the above generated gas and the lower layer liquid of the electrolytic cell were combined, 70% KOH aqueous solution and diisobutylamine were added thereto in equal volumes, and refluxing was conducted for 7 days. The perfluoro product was separated with a separatory funnel, washed with 90% (w/v) acetone aqueous solution containing 10% (w/v) of potassium iodide, then subjected to fractional distillation using an apparatus for fractional distillation equipped with a spinning band column to obtain 44 g (yield 10%) of perfluoro-4-methyloctahydroquinolidine (b.p. 145°–155° C./760 mm Hg). Said compound was confirmed to be the desired compound perfluoro-4-methyloctahydroquinolidine as the result of the infrared absorption psectrum, F nuclear magnetic resonance spectrum, and mass spectrum.

REFERENCE EXAMPLE 2

The following perfluorobicyclo compounds were prepared similarly as in Reference Example 1.

Perfluoro-4-ethyloctahydroquinolidine (b.p. 145°–150° C./760 mm Hg)
perfluoro-2-methyloctahydroquinolidine (b.p. 145°–144° C./760 mm Hg)
Perfluoro-1-methyloctahydroquinolidine (b.p. 145°–155° C./760 mm Hg)
Perfluoro-9a-methyloctahydroquinolidine (b.p. 145°–155° C./760 mm Hg)
Perfluoro-4-ethyloctahydroquinolidine (b.p. 165°–175° C./760 mm Hg)

The present invention is further illustrated below with reference to the Examples and Experimental Examples, but the invention is not limited thereto.

EXAMPLE 1

400 g of vitelline phospholipid was added to 8.5 l of lactic acid added Ringer's solution, and stirred by a mixer to prepare a coarse emulsion, then 2.5 kg of perfluoro-4-methyloctahydroquinolidine was added thereto and stirred vigorously again by the mixer to prepare a coarse emulsion. This coarse emulsion was placed in a liquid tank of a jet emulsifier (manufactured by Manton-Gaulin Co.) and circulated while mantaining the liquid temperature at 50°±5° C. to effect emulsification. The concentration of perfluoro-4-methyloctahydroquinolidine in the obtained emulsion was 27.3% (w/v). The particle diameter as measured by the centrifugal sedimentation method was 0.05–0.25$\mu$. This emulsion was allotted into vials for injection, stoppered and thermally sterilized in a rotary sterilizer, but here was no significant increase in the particle diameter observed.

EXAMPLE 2

An emulsion was obtained by procedures similar to those in Example 1 except that perfluoro-4-methyloctahydroquinolidine was replaced by perfluoro-4-ethyloctahydroquinolidine. The particle diameter of the thus obtained emulsion was 0.05–0.25μ.

EXPERIMENTAL EXAMPLE 1

Stability of Emulsions

Water was added to 20 g of each perfluorobicyclo compound selected in the present invention and 4 g of vitelline phospholipid to make the total volume 200 ml, and emulsification was effected using a Manton-Gaulin emulsifier as used above under nitrogen stream at 200–600 kg/cm$^2$ while maintaining the liquid temperature at 40°–45° C. Each obtained emulsion was filtered through a 0.65μ membrane filter, allotted into 20 ml capacity vials, and, after replacing the atmosphere by nitrogen gas, thermally treated at 100° C. for 30 minutes, followed by storing at 4° C. of room temperature to examine the stability. The particle diameter of the emulsion was measured by the centrifugal sedimentation method by Yokoyama et al [Chem. Pharm. Bull. 22 (12) 2966 (1974)], and from the obtained data, the average particle diameter distribution was calculated using a microcomputer.

Thus, the particle diameter distributions of each perfluorocarbon emulsion before and after heating, and after heating and storing at 4° C. and room temperature (15°–28° C.) are shown in Tables 1 and 2. As is evident from the results, the emulsions according to the present invention are very stable against heating and the influence on the average particle diameter due to heating was not observed at all. Further, when stored at 4° C. after heating, there was no increase in the average particle diameter observed even after 5 months.

TABLE 1

Stability of Perfluoro-4-methyloctahydroquinolidine Emulsion

| | Average Particle Diameter, μ | Distribution of Particle Diameter (wt %) | | | |
|---|---|---|---|---|---|
| | | <0.1μ | 0.1–0.2μ | 0.2–0.3μ | >0.3μ |
| Before heating | 0.122 | 39.0 | 49.9 | 14.2 | 0.9 |
| Immediately after heating | 0.122 | 35.2 | 56.3 | 8.5 | 0 |
| After 2 weeks | | | | | |
| at 4° C. | 0.116 | 37.1 | 59.4 | 3.5 | 0 |
| at R.T.* | 0.127 | 31.2 | 60.1 | 8.7 | 0 |
| After 4 weeks | | | | | |
| at 4° C. | 0.122 | 33.0 | 61.5 | 5.5 | 0 |
| at R.T.* | 0.114 | 31.3 | 68.6 | 0.2 | 0 |
| After 5 months | | | | | |
| at 4° C. | 0.135 | 25.5 | 64.2 | 10.4 | 0 |

*R.T. = Room Temperature

TABLE 2

Stability of Perfluoro-4-ethyloctahydroquinolidine Emulsion

| | Average Particle Diameter, μ | Distribution of Particle Diameter (wt %) | | | |
|---|---|---|---|---|---|
| | | <0.1μ | 0.1–0.2μ | 0.2–0.3μ | >0.3μ |
| Before heating | 0.122 | 38.0 | 51.2 | 10.8 | 0 |
| Immediately after heating | 0.122 | 34.3 | 57.5 | 8.2 | 0 |
| After 2 weeks | | | | | |
| at 4° C. | 0.118 | 37.1 | 61.0 | 1.9 | 0 |
| at R.T.* | 0.128 | 31.3 | 63.5 | 5.2 | 0 |
| After 4 weeks | | | | | |
| at 4° C. | 0.123 | 38.5 | 60.2 | 1.3 | 0 |
| at R.T.* | 0.119 | 34.1 | 60.5 | 5.4 | 0 |
| After 5 months | | | | | |
| at 4° C. | 0.126 | 37.9 | 58.1 | 4.0 | 0 |

*R.T. = Room Temperature

EXPERIMENTAL EXAMPLE 2

Acute Toxicity Test

The acute toxicity test on the preparations of the present invention was carried out using the preparations of the present invention shown in Table 3 which had been physiologically isotonized. The test animals used were Wister-strain male rats (weighing 100–120 g). The emulsion was intravenously administered and the animals were observed for one week after the administration.

The results are such that with either emulsion containing perfluoro-4-methyloctahydroquinolidine or perfluoro-4-ethyloctahydroquinolidine, there was no death case at 100 ml/kg-body weight and thus their toxicity are very small.

TABLE 3

| | Composition | | Ratio % (w/v) |
|---|---|---|---|
| Oil Component (9 vol) | Perfluorobicyclo Compound | | 30 |
| | Emulsifying Agent | Vitelline Phospholipid | 4.0 |
| Electrolyte (1 vol) | | NaCl | 6.00 |
| | | NaHCO$_3$ | 2.1 |
| | | KCl | 0.336 |

TABLE 3-continued

| Composition | | Ratio % (w/v) |
|---|---|---|
| | MgCl$_2$.6H$_2$O | 0.427 |
| | CaCl$_2$.2H$_2$O | 0.356 |
| | D-Glucose | 1.802 |
| pH | 8.0 | |

EXPERIMENTAL EXAMPLE 3

Distribution of Perfluoro-compound in Organs

Using Wister-strain male rats weighing 120-130 g, the emulsion prepared in Example 1 was administered into the tail vein [at 4 g/kg as perfluoro-4-methyloctahydroquinolidine], and for a period of 3 months after the administration, the content of said compound in the liver, spleen and fat tissues due to uptake were measured by means of gas chromatography.

The content of perfluoro-4-methyloctahydroquinolidine uptake in each organ 1, 2 and 4 weeks and 3 months after the administration are shown in Table 4. The compound was taken up in greater amounts by the reticuloendothelial organ shortly after the administration, but soon disappeared rapidly. There was no evidence of adverse influence on the liver or spleen organ.

As a result, the half-life of perfluoro-4-methyloctahydroquinolidine was calculated to be 7.33 days.

TABLE 4

| Organ | Time after the Administration | Residual Rate of perfluorobicyclo compound, % |
|---|---|---|
| Liver | 1 Week | 19.92 |
| | 2 Weeks | 8.66 |
| | 4 Weeks | 1.88 |
| | 3 Months | 0.30 |
| Spleen | 1 Week | 11.61 |
| | 2 Weeks | 9.33 |
| | 4 Weeks | 2.45 |
| | 3 Months | 0.09 |

EXPERIMENTAL EXAMPLE 4

Anatominal Remarks

Wister-strain male rats weighing 120-130 g were administered with 4 g/kg of the perfluorobicyclo-compound emulsion prepared in Example 1 or Example 2, and the dissected organs were observed for a period of 3 months after the administration, and further the organs (liver and spleen) were weighed, to determine the weight relative to the body weight.

One, 2 and 4 weeks and 3 months after the administration of the emulsion, the important organs, i.e. the lung, liver and spleen were observed, to find no evidence of the influence on the organs by either said compound because of their rapid elimination.

What is claimed is:

1. A perfluorobicyclo compound emulsion preparation having oxygen carrying ability comprising 5-50% (w/v) of perfluorobicyclo compound of the general formula

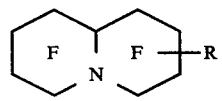

wherein R represents a perfluoromethyl group or perfluoroethyl group, as an oxygen carrying component, 1-5% (w/v) of an emulsifying agent and a balance of a physiologically acceptable aqueous solution, and the emulsion having a particle diameter of 0.3μ or less.

2. A preparation according to claim 1, wherein the perfluorobicyclo compound is perfluoro-4-methyloctahydroquinolidine, perfluoro-2-methyloctahydroquinolidine, perfluoro-1-methyloctahydroquinolidine, perfluoro-9a-methyloctahydroquinolidine, or perfluoro-4-ethyloctahydroquinolidine.

3. A preparation according to claim 1, wherein the emulsifying agent is a polymeric nonionic surfactant or a phospholipid.

4. A preparation according to claim 1, wherein 0.001-0.01% (w/v) of a fatty acid having 8-22 carbon atoms or a physiologically acceptable salt thereof is added as an emulsifying agent.

5. A preparation according to claim 1, wherein an isotonizing amount of an isotonizing agent is added.

6. A preparation according to claim 1, wherein a plasma extender is added.